(12) United States Patent
Uehara et al.

(10) Patent No.: US 7,470,651 B2
(45) Date of Patent: *Dec. 30, 2008

(54) CLEAR CONDITIONING COMPOSITIONS COMPRISING COACERVATE

(75) Inventors: Nobuaki Uehara, Kobe (JP); Robert Lee Wells, Cincinnati, OH (US); Masahiro Hatano, Nishinomiya (JP)

(73) Assignee: The Procter & Gamble Company, Cincinnati, OH (US)

( * ) Notice: Subject to any disclaimer, the term of this patent is extended or adjusted under 35 U.S.C. 154(b) by 154 days.

This patent is subject to a terminal disclaimer.

(21) Appl. No.: 11/471,097

(22) Filed: Jun. 20, 2006

(65) Prior Publication Data

US 2006/0293213 A1    Dec. 28, 2006

Related U.S. Application Data

(60) Provisional application No. 60/697,168, filed on Jul. 7, 2005, provisional application No. 60/693,896, filed on Jun. 24, 2005.

(51) Int. Cl.
*C11D 1/86* (2006.01)
*C11D 3/37* (2006.01)
*C11D 9/36* (2006.01)

(52) U.S. Cl. .............. 510/123; 510/119; 510/124; 510/130; 510/398; 510/417; 510/432; 510/434; 510/466; 510/477; 510/504

(58) Field of Classification Search .............. 510/119, 510/123, 124, 130, 398, 417, 432, 434, 466, 510/477, 504
See application file for complete search history.

(56) References Cited

U.S. PATENT DOCUMENTS

| | | | | |
|---|---|---|---|---|
| 4,210,161 A | | 7/1980 | Wagman | |
| 4,940,576 A | * | 7/1990 | Walsh | 424/70.11 |
| 5,145,607 A | * | 9/1992 | Rich | 510/122 |
| 6,017,860 A | * | 1/2000 | Sajic et al. | 510/124 |
| 6,524,563 B1 | | 2/2003 | Wire | |
| 6,528,046 B1 | * | 3/2003 | Schmenger et al. | 424/70.1 |
| 6,533,873 B1 | * | 3/2003 | Margosiak et al. | 134/42 |
| 6,602,494 B1 | * | 8/2003 | Jahedshoar et al. | 424/70.1 |
| 2001/0027171 A1 | * | 10/2001 | Sajac et al. | 510/124 |
| 2004/0052748 A1 | * | 3/2004 | Vondruska | 424/70.12 |
| 2004/0076595 A1 | * | 4/2004 | Khan | 424/70.11 |
| 2004/0120914 A1 | * | 6/2004 | Decoster et al. | 424/70.12 |
| 2004/0247550 A1 | * | 12/2004 | Asari et al. | 424/70.12 |
| 2005/0175568 A1 | * | 8/2005 | Asari et al. | 424/70.12 |
| 2006/0057097 A1 | | 3/2006 | Derici et al. | |
| 2006/0292104 A1 | * | 12/2006 | Guskey et al. | 424/70.17 |
| 2006/0293197 A1 | * | 12/2006 | Uehara et al. | 510/122 |
| 2007/0010408 A1 | * | 1/2007 | Uehara | 510/119 |
| 2007/0071780 A1 | * | 3/2007 | Dubois et al. | 424/401 |

FOREIGN PATENT DOCUMENTS

| | | |
|---|---|---|
| EP | 1637188 A1 | 3/2006 |
| JP | 54-035222 | 3/1979 |
| JP | 55-130906 | 10/1980 |
| JP | 55-145608 | 11/1980 |
| JP | 61-229813 | 10/1986 |
| JP | 01-313415 | 12/1989 |
| WO | WO-98/18434 A1 | 5/1998 |
| WO | WO-01/35906 A2 | 5/2001 |
| WO | 01/76543  * | 10/2001 |
| WO | WO-01/76543 A1 | 10/2001 |
| WO | PCT/US2006/024759 | 11/2006 |

* cited by examiner

*Primary Examiner*—Charles I Boyer
(74) *Attorney, Agent, or Firm*—Linda M. Sivik; Marianne Dressman; Tara M. Rosnell

(57) ABSTRACT

Disclosed are conditioning compositions comprising by weight: (a) from about 0.1% to about 10% of a surfactant system comprising at least one cationic surfactant; (b) from about 0.05% to about 10% of a polymer selected from the group consisting of an anionic polymer, an amphoteric polymer, and mixtures thereof; and (c) an aqueous carrier; wherein the surfactant system and the polymer form a water-insoluble complex upon dilution, and wherein the composition is transparent or translucent. The compositions are especially suitable for hair care products such as hair conditioning products for rinse-off use.

1 Claim, No Drawings

CLEAR CONDITIONING COMPOSITIONS COMPRISING COACERVATE

CROSS REFERENCE TO RELATED APPLICATION

This application claims the benefit of U.S. Provisional Applications No. 60/697,168, filed on Jul. 7, 2005 and No. 60/693,896, filed on Jun. 24, 2005.

FIELD OF THE INVENTION

The present invention relates to conditioning compositions comprising: a surfactant system comprising at least one cationic surfactant; a polymer selected from the group consisting of an anionic polymer, an amphoteric polymer, and mixtures thereof; and an aqueous carrier; wherein the surfactant system and the polymer form a water-insoluble complex upon dilution; and wherein the composition is transparent or translucent. The compositions are especially suitable for hair care products such as hair conditioning products for rinse-off use.

BACKGROUND OF THE INVENTION

A variety of conditioning compositions such as hair conditioning compositions, skin conditioning compositions, and fabric softeners have been used for a variety of substrates such as hair, skin, and fabric. A common method of providing conditioning benefits is through the use of conditioning agents such as cationic surfactants and polymers, high melting point fatty compounds, low melting point oils, silicone compounds, and mixtures thereof. Most of these conditioning agents are known to provide various conditioning benefits by depositing on the substrates.

Most of the above conditioning agents are also known to make the composition opaque. There is a need for conditioning compositions having a clear product appearance i.e., transparent or translucent product appearance while providing conditioning benefits.

Furthermore, it is still not easy to obtain expected conditioning efficacy from the conditioning agents. It is still not easy to obtain expected deposition of the conditioning agent on the substrates such as hair, skin, and fabric.

Based on foregoing, there remains a desire for conditioning compositions which has a clear product appearance, while providing sufficient conditioning benefits.

None of the existing art provides all of the advantages and benefits of the present invention.

SUMMARY OF THE INVENTION

The present invention is directed to compositions comprising by weight:
(a) from about 0.1% to about 10% of a surfactant system comprising at least one cationic surfactant;
(b) from about 0.05% to about 10% of a polymer selected from the group consisting of an anionic polymer, an amphoteric polymer, and mixtures thereof;
(c) an aqueous carrier;

wherein the surfactant system and the polymer form a water-insoluble complex upon dilution, and wherein the composition is transparent or translucent.

The conditioning composition of the present invention can provide a clear product appearance, while providing sufficient conditioning benefits.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Compositions

The composition of the present invention comprises by weight:
(a) from about 0.1% to about 10% of a surfactant system comprising at least one cationic surfactant;
(b) from about 0.05% to about 10% of a polymer selected from the group consisting of an anionic polymer, an amphoteric polymer, and mixtures thereof; and
(c) an aqueous carrier;

wherein the surfactant system and the polymer form a water-insoluble complex upon dilution, and wherein the composition is transparent or translucent.

The conditioning composition of the present invention can provide sufficient conditioning benefits. Without being limited to the theory, it is believed that; due to the deposition of the water-insoluble complex, i.e., coacervate on the substrates, the composition of the present invention provides sufficient conditioning benefits to wet substrates and the substrates when they are dried.

Without being limited to the theory, it is also believed that; when the composition of the present invention contains conditioning agents, the composition can provide further conditioning benefits due to sufficient deposition of conditioning agents. Without being limited to the theory, it is believed that; one preferred embodiment of the composition of the present invention is that containing conditioning agents which are dispersed in the composition and have a smaller particle size, since such agents are believed to be absorbed or adhered to the surface of the coacervates, or be incorporated into the coacervates, and then effectively deposit on the hair together with the coacervates.

The composition of the present invention may contain additional surfactants other than those used in the surfactant system. When such additional surfactants are included, it is preferred that the total amount of all surfactants in the composition is 10% or less by weight of the composition.

Preferably, the compositions of the present invention are substantially free of anionic surfactants. In the present invention, the compositions being "substantially free of anionic surfactants" means that the compositions include 2% or less, preferably 1% or less of anionic surfactants.

Clear Product Appearance

The conditioning composition of the present invention has a clear product appearance, i.e., transparent or translucent appearance. In the present invention, the composition having a clear product appearance means that the composition has a transmittance of about 25% or more, preferably about 35% or more, more preferably about 40% or more, still more preferably about 50% or more, even more preferably about 60% or more. The transmittances are measured at 600 nm using UV-1601 which is a UV-visible spectrophotometer available from Shimadzu. In view of the desire for clear product appearance, it is preferred that the composition of the present invention has the above transmittance for at least one month, more preferably for at least three months, still more preferably for at least one year at 25° C., following preparation of the composition.

In view of clear product appearance, the compositions of the present invention are preferably substantially free of substantially insoluble oily compounds. In the present invention, the compositions being "substantially free" of substantially insoluble oily compound means that the composition includes 1.0% or less, preferably 0.5% or less, more preferably 0.1% or less, still more preferably 0% of substantially insoluble oily compounds. By "substantially insoluble" oily compound, what is meant is that: the oily compound is substantially insoluble in the compositions at the level used; and the compositions has a transmittance of below about 25%, preferably below about 35%, more preferably below about 40%, still more preferably below about 50%, further more preferably below about 60% at 25° C. when containing the oily compounds at the level used. Such "substantially insoluble" oily compounds are typically those selected from hydrocarbons, fatty compounds, and mixtures thereof. Such hydrocarbons include, for example, poly α-olefin oils, paraffins, waxes, and mixtures thereof. Such fatty compounds include, for example, fatty alcohols such as cetyl alcohol and stearyl alcohol, fatty acids such as stearic acid, fatty alcohol derivatives and fatty acid derivatives such as esters and ethers thereof, and mixtures thereof.

Preferred Embodiments

A preferred embodiment of the present invention is a hair conditioning composition comprising by weight:
(a) from about 0.1% to about 5.0% of a surfactant system comprising a cationic surfactant and a nonionic surfactant;
(b) from about 0.1% to about 5.0% of the polymer selected from the group consisting of an anionic polymer, an amphoteric polymer, and mixtures thereof;
(c) an aqueous carrier; and
(d) from about 0.05% to about 5.0% of a nonionic thickening polymer being substantially soluble in the composition;

wherein the surfactant system and the polymer form a water-insoluble complex upon dilution; wherein the composition is transparent or translucent; wherein the composition is substantially free of substantially insoluble oily compounds.

The above hair conditioning composition preferably further comprises by weight:
(e) from about 0.1% to about 20% of a conditioning agent comprising a silicone compound selected from those having an average particle size of 500 nm or less in the composition, those being substantially soluble in the composition, and mixtures thereof.

Surfactant System

The compositions of the present invention comprise a surfactant system. The surfactant system is included in the compositions at a level by weight of from about 0.1% to about 10%, preferably from about 1% to about 5.0%.

The surfactant system comprises at least one cationic surfactant. The surfactant system can further contain nonionic surfactants, amphoteric surfactants, and/or zwitterionic surfactants. The preferred surfactant system useful herein is selected from the group of consisting of one cationic surfactant, a mixture of two or more cationic surfactants, a mixture of a cationic surfactant and a nonionic surfactant, and mixtures thereof. In view of a clear product appearance, the surfactant system may further contain a co-solvent. Co-solvents useful herein are those described below under the title "CO-SOLVENT". Co-solvents can be contained in the surfactant system at a level by weight of the surfactant system of from about 0.1% to about 50%, preferably from about 5% to about 40%.

Preferably, in view of a clear product appearance, the surfactant system is substantially soluble in the compositions at the level used. By "substantially soluble" surfactant system, what is meant is that the compositions has a transmittance of about 25% or more, preferably about 35% or more, more preferably about 40% or more, still more preferably about 50% or more, even more preferably about 60% or more, at 25° C. when containing the surfactant system at the level used.

Cationic Surfactant

The coacervates of the present invention comprise a cationic surfactant. The cationic surfactant is included in the compositions at a level of from about 0.1% to about 10.0%, preferably from about 0.25% to about 8.0%, more preferably from about 0.5% to about 5.0%.

A variety of cationic surfactants including mono-long alkyl quaternary ammonium salts, di-long alkyl quaternary ammonium salts, hydrophilically substituted mono-long alkyl quaternary ammonium salts, hydrophilically substituted di-long alkyl quaternary ammonium salts, mono-long alkyl chain amines, di-alkyl chain amines can be used in the compositions of the present invention as described below. Among them, preferred are mono-long alkyl chain cationic surfactants such as mono-long alkyl chain quaternary ammonium salts, hydrophilically substituted di-long alkyl quaternary ammonium salts, and mono-long alkyl chain amines. Highly preferred mono-long alkyl chain quaternary ammonium salts are, for example, those in which the mono-long alkyl chain has from 16 to 22 carbon atoms such as cetyl trimethyl ammonium chloride and stearyl trimethyl ammonium chloride. Highly preferred hydrophilically substituted di-long alkyl quaternary ammonium salts are those having at least one ester moieties, and such highly preferred hydrophilically substituted di-long alkyl quaternary ammonium salts includes, for example, dialkyloylethyl hydroxyethyl methyl ammonium salts wherein the alkyl portion of the alkyloylethyl group has from 12 to 22 carbon atoms such as dicocoylethyl hydroxyethyl methyl ammonium salts, distearoylethyl hydroxyethyl methyl ammonium salts, and dipalmitoylethyl hydroxyethyl methyl ammonium salts. Highly preferred mono-long alkyl chain amines are, for example, mono-long alkyl amidoamines having an alkyl group of from about 16 to about 22 carbons such as stearamidopropyldimethylamine.

Among a variety of preferred cationic surfactants, it has been surprisingly found that a mixture of stearyl trimethyl ammonium chloride and stearamidopropyldimethylamine provides improved balance between clarity and conditioning benefits.

Although the above cationic surfactants are preferred in the present invention, other cationic surfactants such as di-long alkyl chain cationic surfactants may also be used alone, or in combination with such preferred cationic surfactants.

Cationic surfactants useful herein include, for example, those corresponding to the general formula (I):

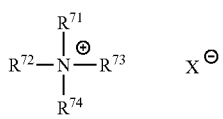

wherein at least one of $R^{71}$, $R^{72}$, $R^{73}$ and $R^{74}$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^{71}$, $R^{72}$, $R^{73}$ and $R^{74}$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^{71}$, $R^{72}$, $R^{73}$ and $R^{74}$ are independently selected from $C_1$ to about $C_{22}$ alkyl.

Among the cationic surfactants of general formula (I), preferred are those containing in the molecule at least one alkyl chain having at least 16 carbons. Non-limiting examples of such preferred cationic surfactants include: behenyl trimethyl ammonium chloride; cetyl trimethyl ammonium chloride; stearyl trimethyl ammonium chloride; olealkonium chloride; hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Also preferred are hydrophilically substituted cationic surfactants in which at least one of the substituents contain one or more aromatic, ether, ester, amido, or amino moieties present as substituents or as linkages in the radical chain, wherein at least one of the $R^{71}$-$R^{74}$ radicals contain one or more hydrophilic moieties selected from alkoxy (preferably $C_1$-$C_3$ alkoxy), polyoxyalkylene (preferably $C_1$-$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, dialkyloylethyl hydroxyethyl methyl ammonium salt, and mixtures thereof; for example, commercially available under the following tradenames; Dehyquart F75, Dehyquart L80, and Dehyquart C4046 from Croda. Babassuamidopropalkonium Chloride available from Croda under the tradename Incroquat BA-85 is also preferably used in the composition.

Amines are suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Nonionic Surfactant

The surfactant system of the present invention can further contain a nonionic surfactant, in view of a clear product appearance. Nonionic surfactants can be included in the compositions at a level of from about 0.1% to 9.9%, preferably from about 0.4% to about 8.0%, more preferably from about 1.0% to about 5.0%, by weight of the composition.

A variety of nonionic surfactants can be used in the compositions of the present invention. Non-limiting examples of nonionic surfactants are described below.

One example of nonionic surfactants useful herein is polyethylene glycol derivatives of glycerides including derivatives of mono-, di- and tri-glycerides and mixtures thereof. One class of polyethylene glycol derivatives of glycerides suitable herein is those which conform to the general formula (I):

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms. Suitable polyethylene glycol derivatives of glycerides can be polyethylene glycol derivatives of hydrogenated castor oil. Such polyethylene glycol derivatives of hydrogenated castor oil include, for example, PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil. Other suitable polyethylene glycol derivatives of glycerides can be polyethylene glycol derivatives of stearic acid. Such polyethylene glycol derivatives of stearic acid include, for example, PEG-30 stearate, PEG-40 stearate, PEG-50 stearate, PEG-75 stearate, PEG-90 stearate, PEG-100 stearate, PEG-120 stearate, and PEG-150 stearate.

Another example of nonionic surfactants useful herein is ethylene glycol ethers of fatty alcohols including any ethylene glycol ethers of fatty alcohols which are suitable for use in a hair conditioning composition. No limiting examples of the ethylene glycol ethers of fatty alcohols include; the ceteth series of compounds such as ceteth-1 through ceteth-45, preferably ceteth-7 through ceteth-20; the isoceteth series of compounds such as isoceteth-20; the steareth series of compounds such as steareth-1 through 100; ceteareth 1 through ceteareth-50; the laureth series of compounds, preferably laureth-7 through Laureth-12; the pareth series of compounds, preferably pareth-9 through pareth-15; propylene glycol ethers of the above ceteth, steareth, ceteareth, and laureth series of compounds, such propylene glycol ethers of ceteth series of compounds including, for example, PPG-5-Ceteth-20; polyoxyethylene ethers or polyoxyethylene-polyoxypropylene ethers of branched alcohols, such branched alcohols including, for example, octyldodecyl alcohol, decyltetradecyl alcohol, dodecylpentadecyl alcohol, hexyldecyl alcohol, and isostearyl alcohol, and such polyoxyethylene-polyoxypropylene ethers of branched alcohols including, for example, POE(20) POP(6) decyltetradecyl ether; and mixtures thereof.

Other nonionic surfactants useful herein include, for example, polysorbates such as polysorbate-20 (POE(20) sorbitan monolaurate) having HLB value of 16.7, polysorbate-21 (POE(4) sorbitan monolaurate) having HLB value of 13.3, polysorbate-40 (POE(20) sorbitan monopalmitate) having HLB value of 15.6, polysorbate-60 (POE(20) sorbitan monostearate) having HLB value of 14.9, polysorbate-61 (POE(4) sorbitan monostearate) having HLB value of 9.6, polysorbate-80 (POE(20)sorbitan monooleate) having HLB value of 15.0, and polysorbate-81 (POE(4) sorbitan monooleate) having HLB value of 10.0.

Preferably, the nonionic surfactants useful herein have an HLB value of from about 8 to about 22, more preferably from about 11 to about 20, still preferably from about 11 to about 18.

Among a variety of nonionic surfactants described above, highly preferred are those selected from the group consisting of isoceteth-20, PPG-5-Ceteth-20, PEG-40 hydrogenated castor oil, polysorbate-20, laureth-20, ceteth-10, ceteth-20, pareth-9 and mixtures thereof.

Amphoteric and Zwitterionic Surfactants

The surfactant system of the present invention can further contain an amphoteric surfactant and/or zwitterionic surfactant. Amphoteric surfactants and/or Zwitterionic surfactants can be included in the compositions at a level of from about 0.1% to 9.9%, preferably from about 0.4% to about 8.0%, more preferably from about 1.0% to about 5.0%, by weight of the composition.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, cocoamphoacetate, cocoamphodiacetate, lauroamphoacetate, lauroamphodiacetate, sodium lauryl sarcosinate, sodium lauroamphoacetate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

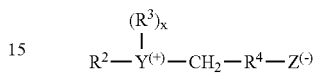

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl)carboxymethyl betaine, oleyl di-methyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the like; amidobetaines and amidosulfobetaines, wherein the RCONH $(CH_2)_3$ radical is attached to the nitrogen atom of the betaine are also useful in this invention.

Anionic or Amphoteric Polymer

The coacervates of the present invention comprise a polymer selected from an anionic polymer, an amphoteric polymer, and mixtures thereof. The polymer is included in the compositions at a level by weight of from about 0.05% to about 10%, preferably from about 0.1% to about 8.0%, more preferably from about 0.25% to about 5.0%, still more preferably from about 0.5% to about 3.0%.

Preferably, in view of a clear product appearance, the polymer is substantially soluble in the compositions at the level used. By "substantially soluble" polymer, what is meant is that the compositions has a transmittance of about 25% or more, preferably about 35% or more, more preferably about 40% or more, still more preferably about 50% or more, even more preferably about 60% or more, at 25° C. when containing the polymer at the level used.

The polymers useful herein are those having a molecular weight of preferably 1000 AMU (Atomic Mass Unit) or more. A variety of anionic polymers and amphoteric polymers can be used in the compositions of the present invention as described below.

Anionic polymers useful herein include, for example: Polyacrylic acid; Polymethacrylic acid; Carboxyvinylpolymer; acrylate copolymers such as Acrylate/C10-30 alkyl acrylate crosspolymer, Acrylic acid/vinyl ester copolymer/ Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer; sulfonate polymers such as Polysulfonic acid, Polystyrene sulphonate, copolymers of methacrylic acid and acrylamidomethylpropane sulfonic acid, and copolymers of acrylic acid and acrylamidomethylpropane sulfonic acid; carboxymethylcellulose; carboxy guar; copolymers of ethylene and maleic acid; and acrylate silicone polymer. Neutralizing agents may be included to neutralize the anionic polymers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available highly preferred anionic polymers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic. In view of clear product appearance and wet conditioning benefits, further preferred are carboxymethylcelluloses.

Amphoteric polymers useful herein include, for example, Polyquaternium-22, Polyquaternium-47, Polyquaternium-39, Octylacrylamide/Acrylates/Butylaminoethyl Methacrylate Copolymer, and Potato Starch modified. Commercially available highly preferred amphoteric polymers include, for example, Polyquaternium-39 having a tradename Merquat Plus 3330 available from Ondeo.

Coacervate

The above surfactant system and the above anionic and/or amphoteric polymers form coacervates which are water-insoluble complexes. The coacervates form upon dilution of the composition, preferably, when the composition is applied to wet substrate and/or rinsed-off with water from the substrate. Preferably, coacervates form when the mass ratio of the composition to water is, preferably by about 1:50, more preferably by about 1:20, still more preferably by about 1:10.

Without being limited to the theory, it is believed that such coacervates provide effective deposition on the substrate since the coacervates are water-insoluble.

Aqueous Carrier

The compositions of the present invention comprise an aqueous carrier. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 40% to about 98%, and more preferably from about 50% to about 98% water.

The pH of the present compositions are preferably from about 2 to about 8, more preferably from about 3 to about 7. Buffers and other pH adjusting agents can be included to achieve the desirable pH.

Thickening Agent

The composition of the present invention preferably contains a thickening agent. Thickening agents useful herein are those which can provide appropriate viscosity and rheology properties to the composition, so that the compositions of the present invention have: (i) a suitable viscosity of preferably from about 1,000 cps to about 150,000 cps, more preferably from about 5,000 cps to about 80,000 cps, still more preferably from about 10,000 cps to about 50,000 cps; and (ii) suitable rheology properties such that the compositions have a Shear Thinning Index (STI) of preferably about 30 or more, more preferably about 50 or more. Preferably, the composition of the present invention has the above viscosity and STI for at least one month, more preferably for at least three months, still more preferably for at least one year at 25° C., following preparation of the composition. The viscosity herein can be suitably measured by Brookfield RVT at a shear rate of $2 \cdot s^{-1}$ at 26.7° C. The Shear Thinning Index (STI) is calculated according to the following equation:

Shear Thinning Index (STI)=a first viscosity/a second viscosity;

wherein the first viscosity is measured at a shear rate of $2 \cdot s^{-1}$, and the second viscosity is measured at a shear rate of $950 \cdot s^{-1}$, both at 26.7° C. by shear rate ramp flow measurement using AR 2000 available from TA Instruments.

Thickening Polymer

The thickening agent is preferably a thickening polymer which is substantially soluble in the composition. By "substantially soluble" thickening polymer, what is meant in the present invention is that the composition has a transmittance of about 25% or more, preferably about 35% or more, more preferably about 40% or more, still more preferably about 50% or more, even more preferably about 60% or more, at 25° C. when containing the thickening polymer at he level used. The composition of the present invention preferably contain a thickening polymer at a level by weight of preferably from about 0.01% to about 10%, more preferably from about 0.05% to about 5%, still more preferably from about 0.1% to about 3%, even more preferably from about 0.5% to about 2%.

A variety of thickening polymers can be used in the compositions of the present invention. Thickening polymers useful herein include, for example, cellulose and its derivatives such as cellulose ethers including hydroxyethylcellulose and hydroxypropylcellulose, hydrophobically modified cellulose ethers such as cetyl hydroxyethylcellulose which is supplied, for example, by Hercules with a tradename Polysurf 67, quaternized celluloses, and hydrophobically modified cationic celluloses; guar polymers including cationic guar polymers and nonionic guar polymers such as Guar Gum 2-hydroxypropyl ether which is supplied, for example, by Rhodia with a tradename Jaguar HP-105; crosslinked polymers such as nonionic crosslinked polymers and cationic crosslinked polymers; and acrylate polymers such as sodium polyacrylate, polyethylacrylate, polyacrylamide, and hydrophobically modified crosslinked cationic acrylates. The thickening polymers useful herein may include the polymers disclosed below under the title "Cationic polymer". Among a variety of thickening polymers, highly preferred are nonionic thickening polymers such as nonionic guar polymers, hydroxyethylcellulose, hydroxypropylcellulose, and hydrophobically modified cellulose ethers such as cetyl hydroxyethylcellulose. Further preferred are hydroxyethylcellulose, hydroxypropylcellulose, and hydrophobically modified cellulose ethers such as cetyl hydroxyethylcellulose. Especially preferred are hydrophobically modified cellulose ethers such as cetyl hydroxyethylcellulose.

Conditionig Agent

The compositions of the present invention preferably contain a conditioning agent. The conditioning agents can be included in the compositions at a level by weight of from about 0.1% to about 20%, more preferably from about 0.1% to about 15%, still more preferably from about 0.25% to about 10%, even more preferably from about 0.5% to about 4.0%.

In view of a clear product appearance while providing conditioning benefits, preferred are those selected from the group consisting of: (i) conditioning agent emulsions having an average particle size of 500 nm or less, preferably 300 nm or less, more preferably 100 nm or less when contained in the composition; (ii) conditioning agents being substantially soluble in the composition; and (iii) mixtures thereof. By "substantially soluble" conditioning agents, what is meant is that the compositions has a transmittance of about 25% or more, preferably about 35% or more, more preferably about 40% or more, still more preferably about 50% or more, even more preferably about 60% or more, at 25° C. when containing the conditioning agents at the level used.

The conditioning agent useful herein include, for example, silicone compounds, glycerin, polyglycerin having a molecular weight of less than about 600,000 AMU, polyglycerin esters having a molecular weight of less than about 600,000 AMU, polyoxyalkylene glycols having a molecular weight of from about 1,000 AMU to about 600,000 AMU such as polyethylene glycols and polypropylene glycols, hydrocarbons, fatty compounds, and mixtures thereof. The conditioning agents useful herein are preferably cationic or nonionic.

Silicone Compound

The conditioning agent used in the present invention is preferably a silicone compound. The silicone compound can be included in the compositions at levels by weight of, preferably from about 0.1% to about 10%, more preferably from about 0.5% to about 8%, still more preferably from about 1% to about 5%.

In view of a clear product appearance while providing conditioning benefits, preferred are those selected from the group consisting of (i) silicone emulsions having an average particle size of 500 nm or less, preferably 300 nm or less, more preferably 100 nm or less when contained in the composition, (ii) silicone compounds being substantially soluble in the composition, and (iii) mixtures thereof. More preferred are silicone compounds being substantially soluble in the composition. By "substantially soluble" silicone compound, what is meant is that the compositions having a about 25% or more, preferably about 35% or more, more preferably about 40% or more, still more preferably about 50% or more, even more preferably about 60% or more, at 25° C. when containing the silicone compound at the level used.

Commercially available silicone emulsions useful herein include, for example, that with a tradename Silicone DC-8177, DC-1870, DC8168, DC8194 and DC7113 available from Dow Corning; quaternized silicone emulsion with a tradename DC5-7133 available from Dow Corning; and amodimethicone emulsion with a tradename XS65-B6413 and SME253 available from General Electric and ADM8020 available from Wacker. Such silicone emulsions may contain a certain level of anionic surfactants. In such case, it is preferred that the composition include 2% or less, more preferably 1% or less of anionic surfactants, as described above under the title "COMPOSITIONS".

With respect to substantially soluble silicone compounds, for example, following materials can be substantially soluble depending on the level of hydrophilic groups in their structure: silicone copolyols such as dimethicone copolyols; amino silicones such as those having a amine content which is high enough to make the amino silicones substantially soluble; amino silicone copolyols such as those having an INCI name Bis (C13-15 Alkoxy) PG Amodimethicone available with a tradename DC2-8500 from Dow Corning; hydrophobically modified amino silicone copolyols; hydrophobically modified amido silicone copolyols such as those having an INCI name PEG-12 Methyl Ether/Lauroxy PEG-5 Amidopropyl Dimethicone available from Dow Corning; and quaternized silicones.

Among the substantially soluble silicone compounds, hydrophobically modified amido silicone copolyols are preferred in view of conditioning benefit especially wet conditioning benefit while providing clear product appearance. Among the hydrophobically modified amido silicone copolyols, highly preferred are those having from about 20% to about 60%, more preferably from about 25% to about 50%, still more preferably from about 30% to about 40% of ethoxylations, in view of the stability in transmittance and/or the stability in viscosity/STI. The percentage of the ethoxylation is calculated according to the following equation: 100×(molecular weight of ethoxyl groups)/(Molecular weight of the silicone compound).

Another preferred substantially soluble silicone compound is silicone copolyols such as dimethicone copolyols in view of improved clarity of product appearance. The silicone copolyols are those being substantially free of hydrophobic substitutions. The hydrophobic substitutions herein are linear or branched, saturated or unsaturated, or functionalized or non-functionalized alkyl group having 6 or more carbon atoms. What meant by being "substantially free of hydrophobic substitutions" is that the silicone compounds contains 1% or less, preferably 0.5% or less, more preferably 0% of hydrophobic substitutions.

Co-Solvent

The compositions of the present invention may contain a co-solvent to help the components such as coacervates, surfactants, and silicone compounds if included, to be substantially soluble in the composition. The co-solvents useful herein are selected from the group consisting of polyhydric alcohols, water soluble alkoxylated nonionic polymers, water-soluble alkyl alcohols and ethers and mixtures thereof. The co-solvents herein can be used at levels by weight of the compositions of preferably from about 0.1% to about 20%, more preferably from about 0.5% to about 20%, still more preferably from about 1% to about 10%.

Polyhydric alcohols useful herein include, for example, glycerin, sorbitol, propylene glycol, butylene glycol, hexylene glycol, ethoxylated glucose, 1,2-hexane diol, hexanetriol, 1,5-pentane diol, dipropylene glycol, erythritol, trehalose, diglycerin, xylitol, maltitol, maltose, glucose, fructose, sodium chondroitin sultate, sodium hyaluronate, sodium adenosin phosphate, sodium lactate, pyrrolidone carbonate, glucosamine, cyclodextrin, octyne diol, diethylene glycol, and mixtures thereof.

Water soluble alkoxylated nonionic polymers useful herein include, for example, polyethylene glycols and polypropylene glycols having a molecular weight of up to about 10,000 AMU such as those with CTFA names PEG-4, PEG-8, PEG-12, PEG-20, PEG-150 and mixtures thereof.

Water soluble alkyl alcohols useful herein include, for example, monohydric C1-C6 alkyl alcohols such as ethanol, isopropyl alcohol, propanol and benzyl alcohol. Water soluble ethers useful herein include, for example, 2-butoxy ethanol, monomethyl ether of diethylene glycol, monoethyl ether of diethylene glycol, monobutyl ether of diethylene glycol.

Among a variety of co-solvents, preferred are 1,2-hexane diol, hexylene glycol, butylene glycol, glycerine, isopropyl alcohol, ethanol, propylene glycol, 1,5-pentane diol, and mixtures thereof.

Cationic Polymer

The conditioning compositions of the present invention may further include cationic polymers, in view of improved product stability, a clear product appearance, and/or increased coacervate formation. The cationic polymers hereof will generally have a weight average molecular weight which is at least about 1,000 AMU, and is less than about 30 millionAMU.

The cationic polymer can be included in the compositions at a level by weight of preferably from about 0.01% to about 10%, more preferably from about 0.05% to about 5%, still more preferably from about 0.05% to about 2.0%.

Suitable cationic polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, NJ, USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, Polyquaternium-7 including that commercially available with tradenames Merquat 550 and Merquat S from Ondeo Nalco; polymethacrylamidopropyl trimonium chloride such as that commercially available with a tradename Polycare 133 from Rhone-Poulenc; and Polyquatemium-37 available from 3V Sigma with tradenames Synthalen CR, Synthalen CU, and Synthalen CN.

Also suitable cationic polymers herein include cationic cellulose derivatives. Cationic cellulose derivative useful herein include, for example, salts of hydroxyethyl cellulose reacted with trimethyl ammonium substituted epoxide, referred to in the industry (CTFA) as Polyquaternium 10, available from Amerchol Corp. (Edison, N.J., USA) in their Polymer JR® and LR® series, and also available from National Starch & Chemical with a tradename Celquat SC-230M; and Polyquaternium-4 with tradename Celquat H-100 available from National Starch & Chemical.

Other suitable cationic polymers include cationic guar gum derivatives, such as guar hydroxypropyltrimonium chloride commercially available from Rhodia in their Jaguar series.

Electrolyte

The compositions of the present invention may contain an electrolyte to control coacervate formation in the composition before dilution. The electrolyte can be used at levels by weight of the compositions of, preferably from about 0.05% or more, more preferably from about 0.1% or more in view of clear product appearance, and preferably about 10% or less, more preferably about 5.0% or less in view of sufficient coacervate formation upon dilution.

The electrolytes useful herein are salts, and such salts useful herein include, for example, chlorides, bromides and nitrates of alkali metals, alkaline earth metals and ammonium. Preferred salts are selected from the group consisting of sodium chloride, sodium bromide, sodium nitrate, potassium chloride, potassium bromide, calcium chloride, magnesium chloride, and ammonium chloride, and mixtures thereof.

Additional Components

The compositions of the present invention may include additional components, which may be selected by the artisan according to the desired characteristics of the final product and which are suitable for rendering the compositions more cosmetically or aesthetically acceptable or to provide them with additional usage benefits. Such additional components generally are used individually at levels of from about 0.001% to about 10%, preferably up to about 5% by weight of the composition.

A wide variety of additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, nonionic surfactants such as glyceryl stearate available from Stepan Chemicals, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate; antidandruff agents such as zinc pyrrithione and salicylic acid; solid particles such as mica, silica, and those with tradenames Unisphere and Unicerin available from Induchem AG (Switzerland); and anti-foaming agent such as that with a tradename XS63-B8929 available from GE-Toshiba Silicone.

Product Forms

The conditioning compositions of the present invention can be in the form of rinse-off products or leave-on products, and can be formulated in a wide variety of product forms, including but not limited to creams, gels, emulsions, mousses and sprays.

The conditioning compositions of the present invention can be used for conditioning a variety of substrates such as hair, skin, and fabric, by applying the compositions to the substrates such as hair, skin, and fabric. The conditioning compositions of the present invention is especially suitable for hair care products such as hair conditioners, skin care products such as skin conditioners, and fabric care products such as fabric softeners.

The conditioning compositions of the present invention are especially suitable for hair conditioners for rinse-off use. Such compositions are preferably used by following steps:
(i) after shampooing hair, applying to the hair an effective amount of the conditioning compositions for conditioning the hair; and
(ii) then rinsing the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

| Compositions (wt %) | Ex. 1 | Ex. 2 | Ex. 3 | Ex. 4 | Ex. 5 |
|---|---|---|---|---|---|
| Anionic polymer-1 *1 | 0.25 | — | 2.0 | — | — |
| Anionic polymer-2 *2 | — | 0.5 | — | 2.0 | 0.25 |
| Cationic surfactant-1 *4 | 1.0 | — | 1.0 | — | 1.0 |
| Cationic surfactant-2 *5 | — | 1.0 | — | 1.0 | — |
| Nonionic surfactant-1 *6 | — | 2.5 | — | 2.5 | 2.5 |
| Nonionic surfactant-2 *7 | 2.5 | — | 2.5 | — | — |
| Thickening polymer-1 *8 | 1.2 | — | — | — | 1.2 |
| Thickening polymer-2 *9 | — | — | 1.4 | — | — |
| Thickening polymer-5 *12 | — | 1.8 | — | 0.5 | — |
| Dimethicone copolyol *13 | 0.5 | 0.5 | — | — | 1.0 |
| Hydrophobically modified amidomethicone copolyol *14 | — | — | 1.0 | 1.0 | — |
| Cationic polymer *15 | 0.5 | — | — | — | — |
| Isopropyl alcohol | 3.0 | 3.0 | — | — | 5.0 |
| Ethanol | — | — | 3.0 | 3.0 | — |
| Methylchloroisothiazolinone/ Methylisothiazolinone *16 | 0.001 | 0.001 | 0.001 | 0.001 | 0.001 |
| NaOH | 0.17 | 0.34 | 1.36 | 1.36 | 0.17 |
| Sodium Chloride | 1.0 | 1.5 | 2.0 | 1.5 | 1.0 |
| Disodium EDTA | 0.13 | 0.13 | 0.13 | 0.13 | 0.13 |
| m-Paraben | 0.2 | 0.2 | 0.2 | 0.2 | 0.2 |
| Perfume | 0.7 | 0.7 | 0.7 | 0.7 | 0.7 |
| Deionized water | q.s. to 100% | | | | |

| | Ex. 6 | Ex. 7 | Ex. 8 | Ex. 9 | Ex. 10 | Ex. 11 | Ex. 12 | Ex. 13 |
|---|---|---|---|---|---|---|---|---|
| Anionic polymer-3 *3 | 0.25 | 1.0 | 1.0 | 0.5 | 0.25 | 1.0 | 1.0 | 1.0 |
| Cationic surfactant-1 *4 | 0.5 | — | — | 1.0 | — | — | 0.4 | — |
| Cationic surfactant-2 *5 | — | 1.0 | 1.0 | — | 1.0 | 1.0 | — | — |
| Cationic surfactant-3 *17 | — | — | — | — | — | — | 1.0 | 1.0 |
| Nonionic surfactant-1 *6 | — | 2.5 | 2.5 | — | 2.5 | — | — | — |
| Nonionic surfactant-2 *7 | 2.5 | — | — | 2.5 | — | 2.5 | 2.5 | 2.5 |
| Thickening polymer-1 *8 | 1.8 | — | — | — | — | — | — | — |
| Thickening polymer-3 *10 | — | 1.5 | 1.4 | — | — | 1.2 | 1.0 | 1.0 |
| Thickening polymer-4 *11 | — | — | — | 1.8 | — | — | — | — |
| Dimethicone copolyol *13 | 0.5 | — | — | — | — | 1.0 | — | — |
| Hydrophobically modified amidomethicone copolyol *14 | — | 2.0 | 2.0 | — | — | — | 2.0 | 0.5 |
| Cationic polymer *15 | 0.5 | — | — | 0.5 | — | — | — | — |
| Citric Acid | — | — | — | — | — | — | 0.3 | 0.3 |
| Ethanol | — | 3.0 | 3.0 | — | — | — | — | — |
| Isopropyl alcohol | 3.0 | — | — | 3.0 | — | 3.0 | — | — |
| Methylchloroisothiazolinone/ Methylisothiazolinone *16 | 0.001 | 0.001 | 0.001 | 0.001 | 0.001 | 0.001 | 0.001 | 0.001 |
| Sodium Chloride | 1.0 | 0.6 | 0.8 | 1.0 | 0.5 | 0.5 | 0.5 | 0.5 |
| Disodium EDTA | 0.13 | 0.13 | 0.13 | 0.13 | 0.13 | 0.13 | 0.13 | 0.13 |
| m-Paraben | 0.2 | 0.2 | 0.2 | 0.2 | 0.2 | 0.2 | 0.2 | 0.2 |
| Perfume | 0.7 | 0.7 | 0.7 | 0.7 | 0.1 | 0.7 | 0.7 | 0.7 |
| Deionized water | q.s. to 100% | | | | | | | |

Definitions of Components
*1 Anionic polymer-1: Carbomer having a tradename Carbopol 980 available from Noveon
*2 Anionic polymer-2: Carbomer having a tradename Carbopol 981 available from Noveon
*3 Anionic polymer-3: Sodium Carboxymethylcellulose having a tradename CMC7M31CFPH available from Hercules
*4 Cationic surfactant-1: Cetrimonium Chloride
*5 Cationic surfactant-2: Stearyltrimonium Chloride
*6 Nonionic surfactant-1: Ceteth-20 having a tradename Nikkol BC-20TX available from Nikko Chemicals
*7 Nonionic surfactant-2: Laureth-9
*8 Thickening polymer-1: Guar Gum 2-Hydroxypropyl Ether having a tradename Jaguar HP-105 available from Rhodia
*9 Thickening polymer-2: Hydroxyethyl ethyl cellulose having a tradename Elfacos CD481 available from Akozo Novel.
*10 Thickening polymer-3: Cetyl hydroxyethyl cellulose having a tradename Polysurf 67 available form Hercules.
*11 Thickening polymer-4: Hydroxyethyl cellulose having a tradename Natrosol from Hercules
*12 Thickening polymer-5: Hydroxypropyl cellulose having a tradename Klucel from CP Kelco
*13 Dimethicone copolyol: Silsoft 810 available from GE Silicone
*14 Hydrophobically modified amidomethicone copolyol: PEG-12 Methyl Ether/Lauroxy PEG-5 Amidopropyl Dimethicone having 22% of ethoxylation
*15 Cationic polymer: Polyquaternium-7 available from Ondeo Nalco with a tradename Merquat S
*16 Methylchloroisothiazolinone/Methylisothiazolinone: Kathon CG available from Rohm&Haas
*17 Cationic surfactant-3: Stearamidopropyldimethylamine Method of Preparation The conditioning compositions of "Ex.1" to "Ex.13" as shown above can be prepared by any conventional method well known in the art. They are suitably made as follows:

Nonionic surfactants are added in water at room temperature, and polymeric materials are added and mixed with vigorous agitation. Then, cationic surfactants, co-solvents, electrolytes, silicone compounds, and other remaining components such as preservatives and perfumes are added, with or without pre-mixing, into the mixture of the nonionic surfactants and polymeric materials with agitation. Alternatively, refractory materials such as m-paraben can be added into the mixture of the nonionic surfactants and polymeric materials at about 60° C. to dissolve such refractory materials. In such case, the mixture is cooled to about 25° C., then cationic surfactants, co-solvents, electrolytes, silicone compounds, and other remaining components such as perfumes are added, with or without pre-mixing, into the mixture with agitation.

Examples 1 through 13 are conditioning compositions of the present invention which are particularly useful for hair conditioners for rinse-off use. These examples have many advantages. For example, the compositions of "Ex.1" through "Ex.13" provide sufficient conditioning benefits. The composition of "Ex.1" through "Ex.13" has a transmittance of 25% or more, and has a clear product appearance.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention.

What is claimed is:

1. A conditioning composition comprising by weight:
   (a) from about 0.1% to about 5.0% of a surfactant system comprising a cationic surfactant and a nonionic surfactant;
   (b) from about 0.1% to about 5.0% of the polymer selected from the group consisting of an anionic polymer, an amphoteric polymer, and mixtures thereof;
   (c) an aqueous carrier;
   (d) from about 0.05% to about 5.0% of a nonionic thickening polymer being substantially soluble in the composition;
   (e) from about 0.1% to about 20% of a conditioning agent comprising a silicone compound being a hydrophobically modified amido silicone copolyol;
   (f) from about 0.1% to about 20% of a co-solvent;
wherein the surfactant system and the polymer form a water-insoluble complex upon dilution; wherein the composition is transparent or translucent; wherein the composition is substantially free of substantially insoluble oily compounds; and wherein the composition has a transmittance of 25% or more.

* * * * *